United States Patent
Stiros et al.

(10) Patent No.: US 7,005,000 B2
(45) Date of Patent: Feb. 28, 2006

(54) AIR DEODORIZATION DEVICE HAVING A DETACHABLE CARTRIDGE MEMBER

(75) Inventors: Paul Stiros, Cincinnati, OH (US); Frank Andrej Kvietok, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 46 days.

(21) Appl. No.: 10/682,633

(22) Filed: Oct. 9, 2003

(65) Prior Publication Data

US 2004/0069147 A1 Apr. 15, 2004

Related U.S. Application Data

(63) Continuation of application No. 10/211,748, filed on Aug. 2, 2002, now abandoned, which is a continuation of application No. PCT/US00/02907, filed on Feb. 4, 2000.

(51) Int. Cl.
*B01D 53/04* (2006.01)

(52) U.S. Cl. ............... 96/135; 96/148; 96/151; 96/153; 55/524

(58) Field of Classification Search .......... 96/134, 96/135, 147, 148, 151, 153, 154; 55/385.4, 55/467, 471, 514, 524, 490, 494, DIG. 13; 62/78
See application file for complete search history.

(56) References Cited

U.S. PATENT DOCUMENTS

| 3,049,399 | A | | 8/1962 | Gamson et al. |
|---|---|---|---|---|
| 3,887,948 | A | | 6/1975 | Stamper |
| 3,972,678 | A | | 8/1976 | Nakshbendi |
| 4,121,916 | A | * | 10/1978 | Fricke ........................ 96/137 |
| 4,161,181 | A | * | 7/1979 | Nicks et al. ................ 131/231 |
| 4,235,750 | A | | 11/1980 | Cazalet |
| 4,604,110 | A | | 8/1986 | Frazier |
| 4,948,567 | A | | 8/1990 | Atarashiya |
| 4,963,166 | A | | 10/1990 | Hoyt et al. |
| 5,288,306 | A | | 2/1994 | Aibe et al. |
| 5,300,139 | A | * | 4/1994 | Lin ............................. 96/135 |
| 5,616,169 | A | | 4/1997 | de Ruiter et al. |
| 5,624,478 | A | | 4/1997 | Patapanian et al. |
| 5,772,738 | A | | 6/1998 | Muraoka |
| 5,858,045 | A | | 1/1999 | Stemmer et al. |
| 6,156,089 | A | | 12/2000 | Stemmer et al. |

FOREIGN PATENT DOCUMENTS

| DE | 3002409 | 7/1981 |
|---|---|---|
| DE | 3640953 | 6/1988 |
| EP | 0311454 | 4/1989 |
| FR | 2189076 | 3/1974 |
| JP | 3251253 | 11/1991 |
| JP | 06288672 | 10/1994 |
| JP | 11047256 | 2/1999 |

* cited by examiner

Primary Examiner—Frank M. Lawrence
(74) Attorney, Agent, or Firm—Thibault Fayette; Kim William Zerby; Steven W. Miller

(57) ABSTRACT

The present invention relates to air deodorizing devices for removing malodor from the air. Such devices are useful for example for storing and preserving food in closed compartments such as refrigerators. The air deodorizing device of the present invention comprises a cartridge member and an air moving member whereby the cartridge member is detachable from the device.

19 Claims, No Drawings

AIR DEODORIZATION DEVICE HAVING A DETACHABLE CARTRIDGE MEMBER

CROSS REFERENCE TO RELATED APPLICATIONS

This application is a continuation of U.S. application Ser. No. 10/211,748 filed Aug. 2, 2002, and now abandoned, which is a continuation of International Application PCT/US00/02907 with an international filing date of Feb. 4, 2000.

FIELD OF THE INVENTION

The present invention relates to air deodorizing devices for removing malodor from the air. Such devices are useful for example for storing and preserving food in closed compartments such as refrigerators.

BACKGROUND

Nowadays, refrigerators have become a common appliance in virtually every household and typically are used for storage and preservation of food, in particular of fresh food such as fruits, vegetables, dairy products, and the like. It is desirable to keep the food items fresh as long as possible in the refrigerator.

It is a well known problem that many food items tend to release malodors into the air which are then captured in the limited air space in a refrigerator. Not only are these malodors unpleasant and offensive to the user of the refrigerator, they can also have a negative impact on the quality of other foods in the refrigerator. For example, it is known that some foods emit strong odors (e.g. fish, boiled eggs, onions, etc.) and that,these odors can transfer to other nearby foods and hurt the taste and freshness of those foods. A common example is transfer of odors into an open container of orange juice or of milk resulting in a noticeable degradation in their taste. It is also well known that malodors from some vegetables (onions, garlic) can transfer to other foods stored within a vegetable drawer. This problem is aggravated when the vegetable drawer is sealed such that there is very little air exchange with the larger compartment of the refrigerator (herein referred to as the "fresh food compartment") and when vegetables have been cut or are stored without any outer wrapping. This problem of odor transfer is particularly acute in the case of ice cubes where odors from the fresh food compartment of the refrigerator can be transferred to the ice in the freezer compartment of the refrigerator. This is especially true in the case of refrigerators in which there is air exchange between the fresh food and freezer compartments, and especially in the case of refrigerators with built-in ice-makers.

U.S. Pat. No. 5,403,548 discloses an activated carbon absorbent to be used for example in refrigerators, shoe boxes, closets, toilets, cars, cupboard, or the like. The activated carbon absorbent is applied in a gas treating apparatus comprising an air inlet, an air outlet, a cylinder housing the activated carbon honeycomb, and a fan aspiring malodor through the air inlet. Change of battery and withdrawal of the cylinder housing the activated carbon are achieved by dismounting the cover of the apparatus. The gas treating apparatus may further comprise an action member for alerting the user to the event that the useful life of the activated carbon adsorbent has run out. This gas treating apparatus has the disadvantages that exchange of batteries and withdrawal of the activated carbon require a multitude of steps including dismounting of the cover and that exchange of battery and activated carbon are carried out separate from each other.

It is therefore an object of the present invention to provide an air deodorizing device which overcomes the disadvantages of the prior art devices.

It is a further object of the present invention to provide an air deodorizing device comprising a replaceable cartridge member housing a filter member whereby the cartridge member is directly accessible from the outside.

It is a further object of the present invention to provide an air deodorizing device comprising a cartridge member housing a replaceable filter member whereby the cartridge member is directly accessible from the outside.

It is a further object of the present invention to provide an air deodorizing device comprising a replacement cartridge member housing a power supply and a filter member.

It is a further object of the present invention to provide an air deodorizing device having a replaceable power supply and a replaceable filter member, the lifetimes of the power supply and the filter member being of the same magnitude.

SUMMARY OF THE INVENTION

The present invention provides an air deodorizing device comprising a cartridge member, the air deodorizing device having an air flow path from an air inlet to an air outlet. The cartridge member comprises a filter member and is arranged with the filter element in interaction with the air flowing along the air flow path. The air deodorizing device further comprises an air moving member for moving air along the air flow path, and is characterized in that the cartridge member is detachable from the air deodorizing device.

DETAILED DESCRIPTION OF THE INVENTION

The device of the present invention is intended to deodorize air, in particular air in confined compartments such as refrigerators, trash bins, cars, closets, and the like.

The cartridge member of the present invention housing the filter member is detachable from the device. The term "detachable" as used herein refers to members which can be easily removed, in particular where no tools such as screw drivers are needed. Preferably, no excessive forces are need for detaching the cartridge means, the cartridge means is directly accessible from the outside, and the cartridge member can be removed by holding the device of the present invention in one hand and by removing the cartridge member with the other hand.

Deodorization of the air in the device of the present invention is achieved by adsorbing the molecules constituting a malodor onto a surface of a filter member. The term "adsorption" is well defined in the art and refers to the adherence of molecules to surfaces which effectively reduces the mobility of these molecules to the two dimensions of the surface. Those molecules remaining in the air will then diffuse so that further molecules come into contact with the surface and subsequently will be adsorbed. Consequently, most of the malodor molecules will travel into the proximity of one of the surfaces at some point in time so that finally most of the malodor will be removed from the air.

A suitable filter member comprises activated carbon for the adsorption. Activated carbon is known to be a very effective filter medium due to its high specific surface area. Whilst activated carbon is very effective as such, the filter member of the present invention may further comprise agents supported on the activated carbon to specifically attack certain malodors such as those comprising S atoms or N atoms. A wide variety of activated carbon based filter media is known in the art. Preferably, the filter members of the present invention comprise at least 2 grams, more preferably at least 5 grams, and most preferably at least 10 grams of activated carbon. Preferably, the filter members of the present invention comprise less than 100 grams, more preferably less than 50 grams, yet more preferably less than 40 grams, and most preferably less than 30 grams of activated carbon.

The filter member of the present invention comprises an air inlet, an air outlet, and an air flow path through the filter member from the air inlet to the air outlet. The filter medium is disposed in the filter member of the present invention such that it comes into contact with the air flowing along the air flow path. The filter medium may be arranged as a flow by filter or as a flow through filter. The filter member of the present invention may comprise a support for the filter medium for example in the form of a foam, a nonwoven material or a woven material. Preferably, the activated carbon is supported on a polyurethane foam having an activated carbon density of at least 0.01 grams per $cm^3$, more preferably of at least 0.05 grams per $cm^3$, and most preferably of at least 0.1 grams per $cm^3$ and having an activated carbon density of less than 0.3 grams per $cm^3$.

The deodorization of the air in the device of the present invention is enhanced by increasing the air flow through the filter member by means of an air moving member. Preferably, the air moving means moves at least 100 ml of air per second through the air inlet into the device, more preferably at least 200 ml/s, most preferably at least 300 ml/s. There are known in the art a wide variety of suitable air moving members such as for example fans and blowers. A particularly suitable fan is a centrifugal fan. A suitable member for driving the fan is a small motor, for example a DC motor available from MABUCHI MOTOR CO.,LTD., Japan, under the designation of RF-330TK. The air moving members of the present invention may be powered electrically. Many electrical power sources could be imagined including domestic AC electrical power or power from a static power supply. Alternatively and preferably electrical power may be supplied by means of a battery, preferably a dry alkaline cell battery, or a rechargeable battery. The electrical power may also be received from a solar cell. Any replaceable power supply preferably is designed to last at least one month, more preferably at least two months, yet more preferably at least three months, most preferably at least four months.

To improve the malodor removal performance and to simplify the mechanical construction of the air deodorizing device of the present invention, the filter member and the air moving member are preferably arranged such that substantially all air aspired by the air moving member is forced to flow through the filter member before it penetrates the air inlet of the air moving member. In other words, the air inlet of the cartridge member is unitary with the air inlet of the air deodorizing device. In this setup, only one air path connection is needed between the filter member and the air member and hence complexity is decreased. Furthermore, withdrawal of the cartridge member is greatly simplified if only one connection has to be disengaged. Any disengageable air flow connection may of course comprise sealing members to improve air flow performance. Any such connection may further comprise a mechanical engaging members to stabilize the connection.

The filter member of the present invention may be replaced by detaching the cartridge member from the device of the present invention and inserting in a new one. It is to be understood in this context that the present invention includes embodiments in which the cartridge member as a whole comprising a filter member is replaced and further includes embodiments in which the cartridge is reused and contains a replaceable filter element.

Preferably, the cartridge member of the present invention is directly accessible from the outside of the device without the need to unmount any covers or the like. More preferably, the cartridge member can simply be lifted off from the device. For example, the cartridge member may simply be sitting on top of the air moving member only held in place by gravitational forces whereby the surface topology of the interfacing parts of the cartridge member and the air moving member match each other such as in a hemispherical design.

Optionally, the cartridge member of the present invention may further comprise the power supply for the air moving member. In this case, the interface between the cartridge member and the air moving member needs to comprise electrical contacts connecting the power supply with the drive member of the air moving member.

Preferably, the lifetime of the filter member and the lifetime of the power supply are substantially equal so that both members may be replaced at the same time intervals. In this case, an empty power supply would also signal that the filter element has to be replaced.

The air deodorizing device of the present invention may comprise a signal member to indicate if the life span of the filter member has run out. The signal member may be slaved to the time the filter member has been exposed to air or may be slaved to the overall runtime of the air moving member. In case the power supply for the air moving member is included in the filter member and accordingly is replaced with the filter member, the signal member may be slaved to the remaining charge of the power supply thus indicating that filter member and power supply needs to be replaced.

What is claimed is:

1. An air deodorizing device having an air flow path from an air inlet to an air outlet, said deodorizing device comprising:

a) a cartridge member detachable from a portion of said deodorizing device, said cartridge member comprising a filter member having an air inlet and an air outlet, wherein said cartridge member is adapted to be arranged with respect to said portion of said deodorizing device such that said filter member comes into contact with the air flowing along said air flow path of said deodorizing device; and b) an air moving member for moving air along said air flow path, said air moving member comprising a fan connected to an electric motor wherein said electric motor is powered by a source of electricity and wherein said air moving member is adapted to displace at least 100 ml of air per second through the air inlet of said deodorizing device, and wherein said cartridge member is adapted to be positioned above said air moving member when said air moving member moves air along said air flow path and wherein a surface topology of parts of said cartridge member and said air moving member match each other, wherein said surface topology comprises a hemispherical design.

2. A refrigerator air deodorizing device according to claim 1.

3. The air deodorizing device according to claim 1 wherein said cartridge member is directly accessible from the outside of said deodorizing device.

4. The air deodorizing device according to claim 1 wherein said filter member comprises activated carbon.

5. The air deodorizing device according to claim 4 wherein said activated carbon is supported on a support member, said support member comprising a foam, a woven, or a nonwoven web material.

6. The air deodorizing device according to claim 5 wherein said activated carbon is supported on a polyurethane foam and has a carbon density of from 0.01 to 0.3 grams per cm$^3$.

7. The air deodorizing device according to claim 4 wherein said filter member comprises between 5 and 30 grams of activated carbon.

8. The air deodorizing device of claim 1 wherein said cartridge member is adapted only to be held in place with respect to said air moving member by gravitational forces.

9. An air deodorizing device having an air flow path from an air inlet to an air outlet, said deodorizing device comprising:
   a) a cartridge member detachable from a portion of said deodorizing device, said cartridge member comprising a filter member having an air inlet and an air outlet, said cartridge member being arranged within an area of said deodorizing device such that said filter member comes into contact with the air flowing along said air flow path of said deodorizing device; and
   b) an air moving member for moving air along said air flow path, said air moving member comprising a fan connected to an electric motor wherein said electric motor is powered by a source of electricity and wherein said air moving member is adapted to displace at least 100 ml of air per second through the air inlet of said deodorizing device and wherein a surface topology of parts of said cartridge member and said air moving member match each other, wherein said surface topology comprises a hemispherical design.

10. The air deodorizing device according to claim 9 wherein said source of electricity is a battery, wherein said battery is located within said cartridge member and wherein said battery and said filter member have substantially equal lifetimes.

11. The air deodorizing device according to claim 9 wherein said filter member is located between the air inlet of said deodorizing device and said air moving member such that substantially all the air aspired by said air moving member is forced to flow through said filter member along said air flow path.

12. The air deodorizing device of claim 9, wherein only a single air path connection exists between the said filter member and said air moving member wherein substantially all air aspired by said air moving member is forced to flow through said filter member before it penetrates an inlet of said air moving member.

13. The air deodorizing device of claim 9, wherein said air inlet of said cartridge member is unitary with said air inlet of said air deodorizing device wherein substantially all air aspired by said air moving member is forced so flow through said filter member before it penetrates an inlet of said air moving member.

14. An air deodorizing device having an air flow path from an air inlet to an air outlet, said deodorizing device comprising:
   a) a cartridge member detachable from a portion of said deodorizing device, said cartridge member comprising a filter member having an air inlet and an air outlet, wherein said cartridge member is adapted to be arranged with respect to said portion of said deodorizing device such that said filter member comes into contact with the air flowing along said air flaw path of said deodorizing device; and
   b) an air moving member for moving air along said air flow path, said air moving member comprising a fan connected to an electric motor wherein said electric motor is powered by a source of electricity and wherein said air moving member is adapted to displace at least 100 ml of air per second through the air inlet of said deodorizing device,
   wherein interfacing parts of said cartridge member and said air moving member include a hemispherical surface topology that match each other and wherein the cartridge member is adapted to rest above the air moving member such that the cartridge member is only held In place by gravitational forces.

15. The air deodorizing device according to claim 14 wherein said cartridge member is directly accessible from the outside of said deodorizing device.

16. The air deodorizing device according to claim 14 wherein said filter member comprises activated carbon.

17. The air deodorizing device according to claim 16 wherein said activated carbon is supported on a support member, said support member comprising a foam, a woven, or a nonwoven web material.

18. The air deodorizing device according to claim 17 wherein said activated carbon is supported on a polyurethane foam and has a carbon density of from 0.01 to 0.3 grams per cm$^3$.

19. The air deodorizing device according to claim 16 wherein said filter member comprises between 5 and 30 grams of activated carbon.

\* \* \* \* \*